(12) United States Patent
Jennings et al.

(10) Patent No.: US 6,320,170 B1
(45) Date of Patent: Nov. 20, 2001

(54) MICROWAVE VOLATILES ANALYZER WITH HIGH EFFICIENCY CAVITY

(75) Inventors: William Edward Jennings, Wingate, NC (US); Matthew Donald Barrett, Columbia, SC (US); Edward Earl King, Charlotte, NC (US)

(73) Assignee: Cem Corporation, Matthews, NC (US)

( * ) Notice: Subject to any disclaimer, the term of this patent is extended or adjusted under 35 U.S.C. 154(b) by 0 days.

(21) Appl. No.: 09/398,129

(22) Filed: Sep. 17, 1999

(51) Int. Cl.[7] ................................. H05B 6/80; G01N 5/04
(52) U.S. Cl. ...................... 219/679; 219/756; 219/711; 219/708; 219/746; 219/705; 73/54.42; 73/76; 374/14; 374/149
(58) Field of Search ..................................... 219/679, 710, 219/711, 746, 756, 750, 705, 708; 73/54.42, 61.46, 61.76, 76; 374/14, 141, 149, 142

(56) References Cited

U.S. PATENT DOCUMENTS

| | | |
|---|---|---|
| 3,252,115 | 5/1966 | Gordon . |
| 3,461,261 | 8/1969 | Lewis et al. . |
| 3,590,201 | 6/1971 | Basinger . |
| 3,590,202 | 6/1971 | Day et al. . |
| 3,890,825 * | 6/1975 | Davis ................................... 219/708 |
| 4,006,338 * | 2/1977 | Dehn .................................... 219/746 |
| 4,343,976 | 8/1982 | Nasretdin et al. . |
| 4,413,168 | 11/1983 | Teich . |
| 4,438,500 | 3/1984 | Collins et al. . |
| 4,457,632 | 7/1984 | Collins et al. . |
| 4,562,409 | 12/1985 | Saito et al. . |
| 4,883,570 | 11/1989 | Efthimion et al. . |
| 4,908,486 * | 3/1990 | Fry ....................................... 219/746 |
| 5,250,773 | 10/1993 | Lind et al. . |
| 5,280,216 | 1/1994 | Mourier . |
| 5,308,944 | 5/1994 | Stone-Elander et al. . |
| 5,351,541 | 10/1994 | Petrovich et al. . |
| 5,459,302 * | 10/1995 | Jacquault .............................. 219/711 |
| 5,632,921 | 5/1997 | Risman et al. . |
| 5,725,951 | 3/1998 | Schuette et al. . |
| 5,796,080 * | 8/1998 | Jennings et al. ...................... 219/711 |
| 5,834,744 * | 11/1998 | Risman ................................. 219/746 |
| 6,072,168 * | 6/2000 | Feher et al. ........................... 219/695 |
| 6,084,226 * | 7/2000 | Greene et al. ........................ 219/710 |

FOREIGN PATENT DOCUMENTS

| | | |
|---|---|---|
| 196 33 245 * | 11/1997 | (DE) . |
| WO99/40409 | 8/1999 | (WO) . |

OTHER PUBLICATIONS

Varlamova N. A. et al: "On the Quality Factor of Cavity Resonators of Different Shapes", Telecommunications and Radio Engineering, US, Begell House, Inc., New York, NY, Vol. 52, No. 2, 1998, pp. 79–85.*

* cited by examiner

Primary Examiner—Philip H. Leung
(74) Attorney, Agent, or Firm—Summa & Allan, P.A.

(57) ABSTRACT

A volatiles analyzer is disclosed that includes a source of microwave radiation that can selectively produce at least one predetermined frequency of microwave radiation. A cavity is in communication with the source. The analyzer includes an analytical pan balance with at least its balance pan in the cavity. The walls of the cavity form a polyhedron that focuses microwave energy of the predetermined frequency on the balance pan while supporting a plurality of TM and TE modes in the cavity.

21 Claims, 10 Drawing Sheets

MICROWAVE VOLATILES ANALYZER WITH HIGH EFFICIENCY CAVITY

FIELD OF THE INVENTION

The present invention relates to analytical chemistry techniques and instruments, and particularly those used for analyzing the volatiles content of materials. In particular, the invention relates to the use of microwave energy to drive moisture or other volatiles from substances so that the moisture content (or in complimentary fashion the solids content) can be quickly and accurately measured.

BACKGROUND OF THE INVENTION

The analysis of the volatiles content of materials is one of the most common types of testing carried out on a wide variety of materials. In its most fundamental sense, the measurement of the volatile (very often the moisture) content of a material is usually carried out by taking a representative sample of the material, weighing it, drying it, and then reweighing it after the drying process. The difference between the starting weight and the ending weight, when divided by the starting weight and expressed as a percentage, is the percentage of volatile content. The procedure is based on differential weighing and is somewhat formally referred to as gravimetric moisture determination.

As a preliminary matter, it is well-understood in this art that the results of such differential weight analysis can be calculated and expressed either as the percentage of volatiles that leave a sample, or as the percentage of solids that remain. The manipulative steps, however, are the same. Thus, devices of the type described herein are often described as "moisture/solids" analyzers.

Furthermore, although the term "moisture" is used most frequently herein, it will be understood that the apparatus and methods disclosed and claimed herein apply to any volatile species that can be driven from a heated sample in a differential weighing technique.

For many years, moisture analysis of this type has been carried out by heating the respective samples in conventional conduction or convection-type ovens. The process is generally time consuming for several reasons. First, in order to make sure that all of the moisture has been driven from a sample, the heating and re-weighing process must be carried out several times until the difference in dry weights are either eliminated, or so small as to be within measurement accuracy limits. Because conventional drying is relatively time consuming, the need to take several repeated measurements on the same sample is similarly time consuming.

As another factor, the analytical balances typically used to weigh the samples are usually pan-type balances; i.e., they include a flat surface upon which the sample (and sometimes its container) are placed and which is in turn attached to a sensitive balancing mechanism. Under these circumstances, when a warm object such as a heated sample is placed on a balance pan, the warm object tends to set up a flow of convection air currents in the immediate vicinity. In turn, these upwardly flowing currents tend to lift the balance pan and produce an inaccurate reading. Generally, the more sensitive the balance, the more likely, or the greater amount proportionally by which, the reading will be in error. Thus, in addition to the time required to conventionally heat a sample to dryness on a repeated basis, there also exists the need to allow the sample to cool sufficiently to avoid creating convection currents in the balance. Thus, convection and conduction methods of moisture analysis tend to be relatively time consuming.

More recently, microwave energy has been used to help speed up the drying process. In these techniques, microwaves are used to drive the moisture from the sample rather than conventional convection or conduction heating. Microwaves offer several advantages in this respect, the most direct being the fact that they heat water or other volatiles directly, rather than by conduction through the material itself. Stated differently, microwaves immediately interact with the moisture in a sample and tend to volatize it quickly. Furthermore, because microwaves affect only certain types of substances within a sample (generally polar substances), they tend to heat the overall sample less than do conventional convection and conduction techniques. As a result, microwave heating can hasten moisture analysis by several orders of magnitude. By way of example, different manufacturers of microwave drying devices point out that processes that can take as many as 16 hours for moisture analysis (e.g., ground beef) can be done in a conventional microwave device in about 5 minutes. Additionally, even those materials which can be dried relatively quickly in conventional ovens, can still be greatly accelerated in a microwave device. For example, according to published information, tomato paste (which has a moisture level of about 77.55%) can be dried in a conventional oven in about 1.5 hours. In contrast, it can be dried in a conventional microwave device in about 5 minutes. Other materials, such as cheese, can be analyzed in a conventional microwave drying device in as little as 3.5 minutes.

Accordingly, the microwave moisture analyzer has become a widely accepted piece of apparatus in many chemical laboratories. An exemplary version is the Lab Wave-9000 microwave moisture/solids analyzer from CEM Corporation, the assignee of the present invention, which combines an analytical balance with its microwave drying capability. Devices such as the Lab Wave-9000 are also typically operated in conjunction with microprocessors and related electronic circuits. The processor's operation and logic (software) enable the moisture content to be calculated even more quickly using generally well understood relationships between weight loss over a given period of time and the ultimate moisture content of a given sample.

Nevertheless, the wide acceptance of microwave drying devices such as the Lab Wave-9000 has driven further innovation and a desire to carry out drying processes even more quickly and efficiently. Accordingly, newer types of microwave devices are appearing in the marketplace which attempt to focus microwave energy more carefully and efficiently in an attempt to dry materials more quickly, more accurately, and using less power.

Some newer versions of microwave drying devices tend to follow the disclosures of U.S. Pat. No. 5,632,921 to Per O. Risman. The Risman patent describes a generally cylindrical microwave cavity device in which the modes of microwave energy are carefully controlled to give a heating effect. Based on public disclosures, and without attempting to speak for the respective manufacturers, the "Moistwave" system from Prolabo (France) and the "M2" microwave moisture/solids analyzer from Denver Instruments (Arvada, Colo., USA) appear to follow the Risman patent in their use of specifically cylindrical cavities. According to advertising materials for both of these devices, they are able to reduce even the ordinary microwave drying time by a significant fraction, for example taking drying steps that require 3, 4, or 5 minutes in a conventional microwave device, and carrying them out in about 1 or 2 minutes or less. As set forth in the Risman '921 patent, however, these devices operate on a very carefully selected combination of limited transverse magnetic modes.

The Denver Instruments device also appears to follow some or all of the disclosures of published International Application WO 99/40409 corresponding to International Application PCT/US01866.

Accordingly, a need exists for further improvement in the area of high-efficiency microwave moisture analyzers.

OBJECT AND SUMMARY OF THE INVENTION

Therefore it is an object of the present invention to provide a microwave volatiles (or "moisture/solids") analyzer that is efficient and thorough in its analysis, while minimizing the amount of energy and physical space that it uses.

The invention meets this object with a volatiles (moisture) analyzer that comprises a source of microwave radiation that can selectively produce at least one predetermined frequency of microwave radiation. A cavity is in communication with the source, and an analytical pan balance is also part of the analyzer and has at least its balance pan in the cavity. The walls of the cavity form a polyhedron that focuses microwave energy of the predetermined frequency on the balance pan while supporting a plurality of TM and TE modes in the cavity.

In another aspect, the invention is a cavity for a microwave device in which the cavity comprises a polyhedron in which at least eight of the faces of the polyhedron form a regular octagon.

In yet another aspect, the invention is a moisture analyzer that includes a source of microwave radiation that can selectively produce at least one predetermined frequency of microwave radiation. A cavity is in communication with the source, and an analytical pan balance has at least its balance pan in the cavity. The cavity comprises a polyhedron with more than six faces.

These and other objects and advantages of the invention will be more clearly understood when taken in conjunction with the detailed description and with the accompanying drawings in which:

DETAILED DESCRIPTION OF THE PREFERRED EMBODIMENTS

Figure 1:
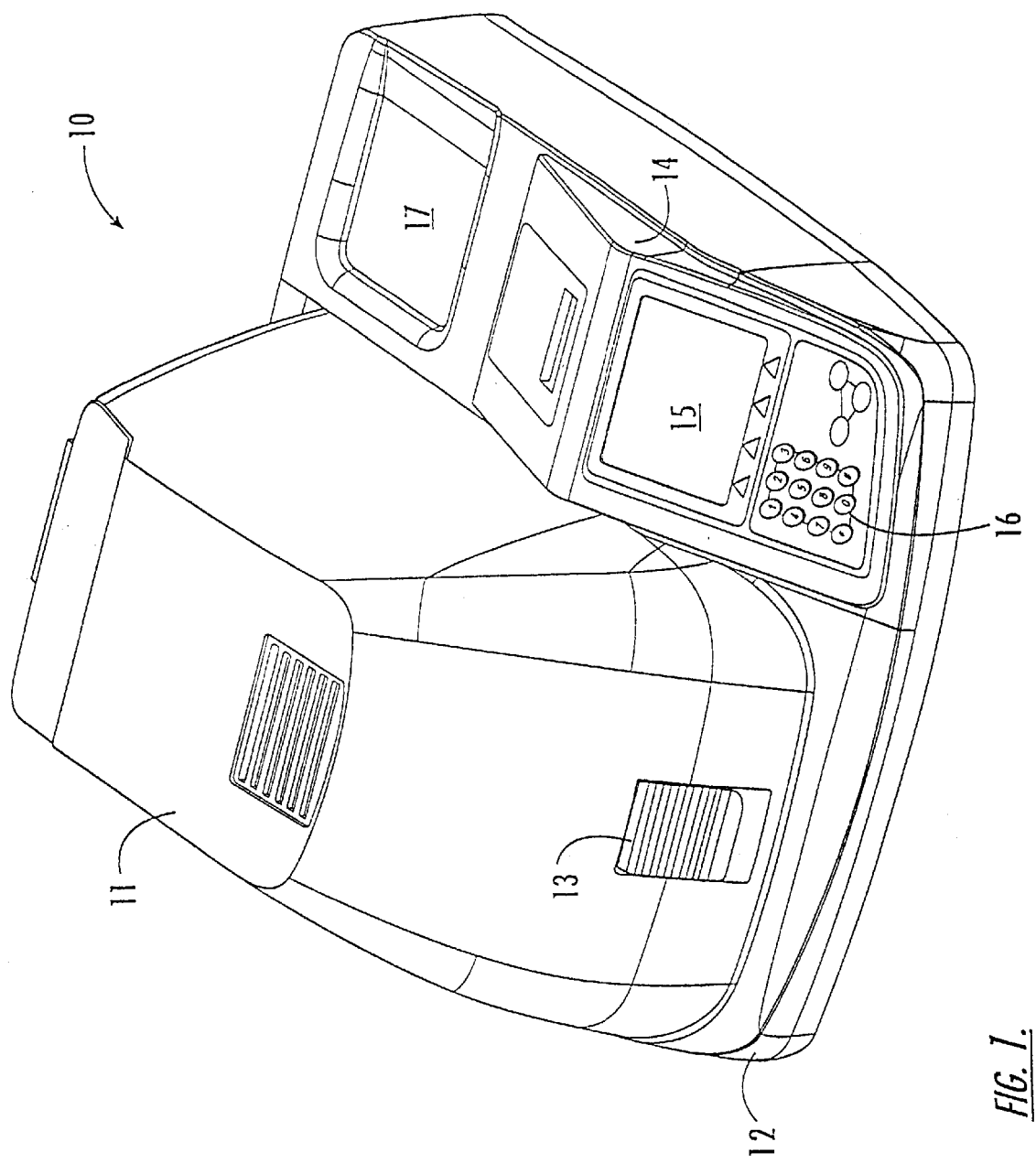
FIG. 1 is a perspective view of a commercial embodiment of a volatiles analyzer according to the present invention.

FIG. 1 is a perspective view of a commercial embodiment of the present invention broadly designated at 10. The microwave portions of the device are in inost circumstances kept under a cover 11 and will be described in more detail with respect to the other figures. The cover 11 is secured to a base 12 by a latch 13. FIG. 1 also shows the housing 14 for any microprocessors used in conjunction with the device, along with a display 15 and a keyboard entry pad 16. In the embodiment shown in FIG. 1, the indented portion 17 near the rear of the device 10 is shaped to hold a number of sample pads of the type that are typically used in this type of moisture analysis.

Figure 2:
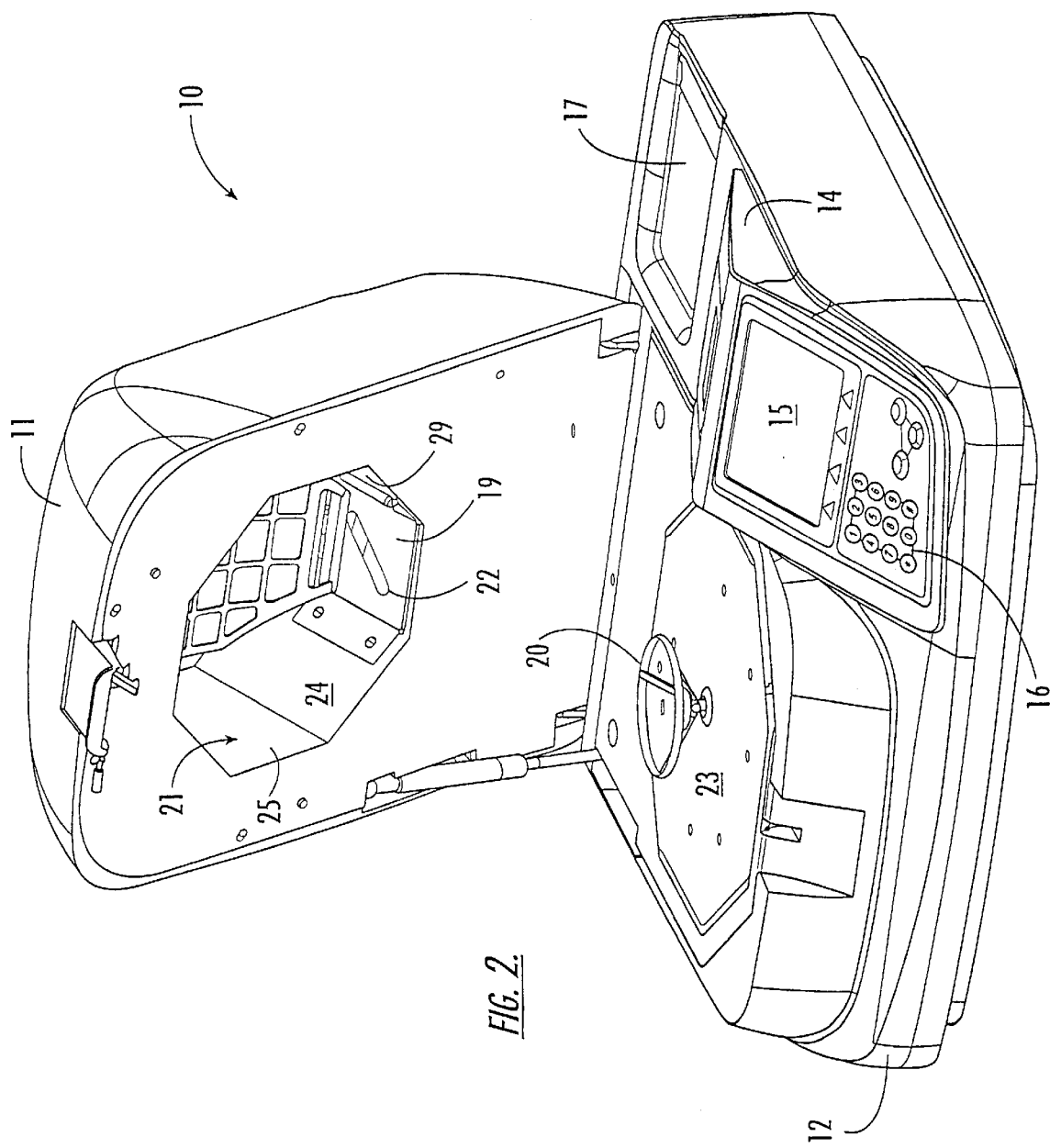
FIG. 2 is another perspective view of the volatiles analyzer of the present invention and showing it in the open position along with portions of the interior of the cavity.

FIG. 2 shows the volatiles analyzer 10 of the present invention in an open position. FIG. 2 illustrates that the invention includes an analytical pan balance of which at least the balance pan 20 is present in the cavity. It will be understood that the term "balance pan" is used in its broadest sense and does not literally have to be a pan. Instead, as illustrated in FIG. 2 and elsewhere, the pan is preferably formed of a framework, often of a material such as plastic, that is substantially permeable or even transparent to microwave radiation so as not to otherwise interfere with the processes of the device. In a typical operation, a sample pad (not shown) is placed on top of the pan 20 and a sample is in turn placed on top of the sample pad. For some materials, a second sample pad is placed over the sample to prevent splattering during the heating process. The preferred sample pads are preferably formed of glass fibers, although any material is acceptable that does not otherwise interfere with the microwaves or other aspects of the process.

The nature and operation of analytical balances are generally well understood in the chemical arts and will not be described in detail herein. The balance should be selected so as to avoid interfering with the propagation of microwaves in the cavity in any undesired fashion. Various balances are available from, or can be readily custom-designed by, manufacturers such as Mettler Toledo (Mettler Toledo International, Inc., Worthington, Ohio, USA). Some such balances can measure with an accuracy approaching 0.0000001 gram (g). For most moisture determinations on small samples an accuracy of 0.0001 g (i.e., 0.1 milligram) is preferred.

FIG. 2 also shows the cavity broadly designated at 21 which in the invention forms a polyhedron that focuses microwave energy of the predetermined frequency generated by the source (FIG. 3) on the balance pan 20 while supporting a plurality of TM and TE modes in the cavity. By focusing the energy on the balance pan—i.e., on the pan's geometric position in the cavity—the invention greatly enhances the efficiency of the heating process, even though the cavity itself is much smaller than in earlier devices.

FIG. 2 also shows the port 22 that permits entry of microwave energy from the waveguide (FIG. 3) into the cavity 21. In preferred embodiments, the port 22 is the sole entry for microwaves between the waveguide and the cavity 21. As perhaps best understood by a combination of FIGS. 2 and 3, in preferred embodiments the waveguide 23 is a rectangular solid and the port 22 is a longitudinal slot positioned in one face of the waveguide 21 and oriented neither parallel nor perpendicular to any of the angles forming the rectangular solid waveguide.

FIG. 2 also illustrates that the invention can be understood in another sense as a cavity for a microwave device that comprises a polyhedron in which eight of its faces form a regular octagon. The words "polyhedron," "octagon," and "regular" are all used in their ordinary and dictionary sense in this specification and in the claims. Thus, a polyhedron is a three-dimensional geometrical solid with a plurality of planar faces. An octagon is a two-dimensional figure with eight linear sides. A regular octagon is an eight-sided two-dimensional figure in which each of the eight sides are equal in length and all of the eight angles are equal to one another.

FIG. 2 also shows that in the illustrated embodiment, one face is a regular octagon illustrated as 23 and comprises the bottom face of the cavity 21. FIG. 2 also illustrates that in the preferred embodiment, the polyhedron has 12 sides, eight of which (19, 24, 25, 29–31, and 38–39) are both joined to and perpendicular to the regular octagon face 23. As perhaps best illustrated in FIG. 3, the polyhedron cavity also includes two faces, 26 and 28 that are both nonparallel and nonperpendicular to the other ten faces of the 12-sided polygon. The parallel face 27 (i.e., parallel to the regular octagon face) is joined to two of the perpendicular faces that are respectively parallel to one another, the nonparallel and nonperpendicular faces are each joined to the parallel face 26, and the nonparallel and nonperpendicular faces are each joined to the perpendicular faces. As FIG. 2 illustrates, the eight sides 19, 24, 25, 29–31, and 38–39 form a regular octagon regardless of the top and bottom geometry of the cavity 21.

Although the illustrated embodiment shows the bottom face 23 as being planar and a regular octagon, the invention is not limited to such an arrangement, and the bottom portion of the cavity could be nonplanar. Those familiar with the propagation of microwave energy will recognize that the modes and focusing of the microwaves depend on the waveguide, the port from the waveguide to the cavity, and the cavity geometry, and not upon visual references or orientations such as "up" or "down" or the "top," "bottom," or "sides" of the cavity. Such terms are used herein in conjunction with the drawings to illustrate the invention rather than to limit its scope.

FIG. 2 also shows a number of items that are the same as and were described with respect to FIG. 1, and that will not be otherwise described with respect to FIG. 2.

Figure 3:
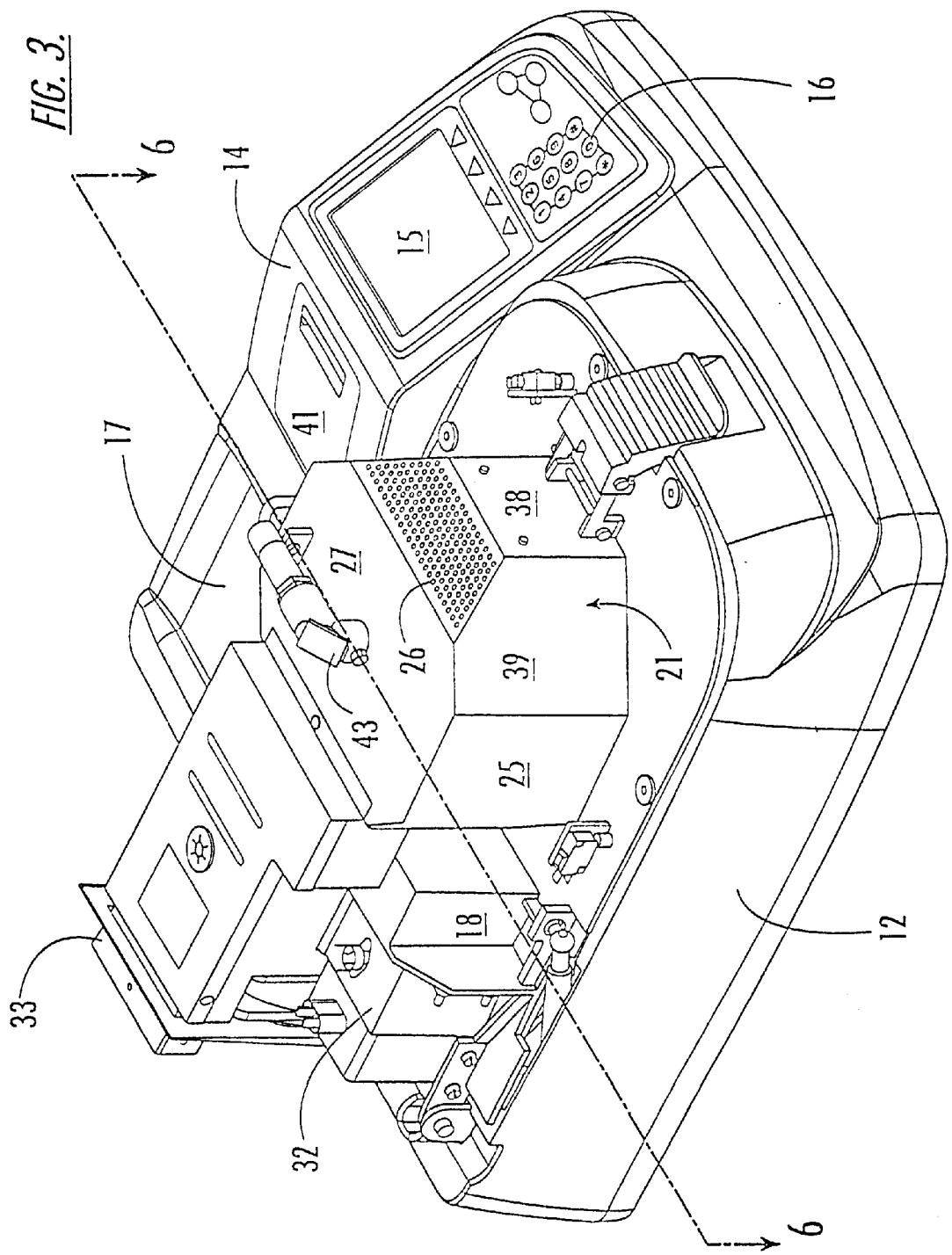
FIG. 3 is a perspective view of the volatiles analyzer of the present invention without the cover and showing some of the internal parts.
Figure 4:
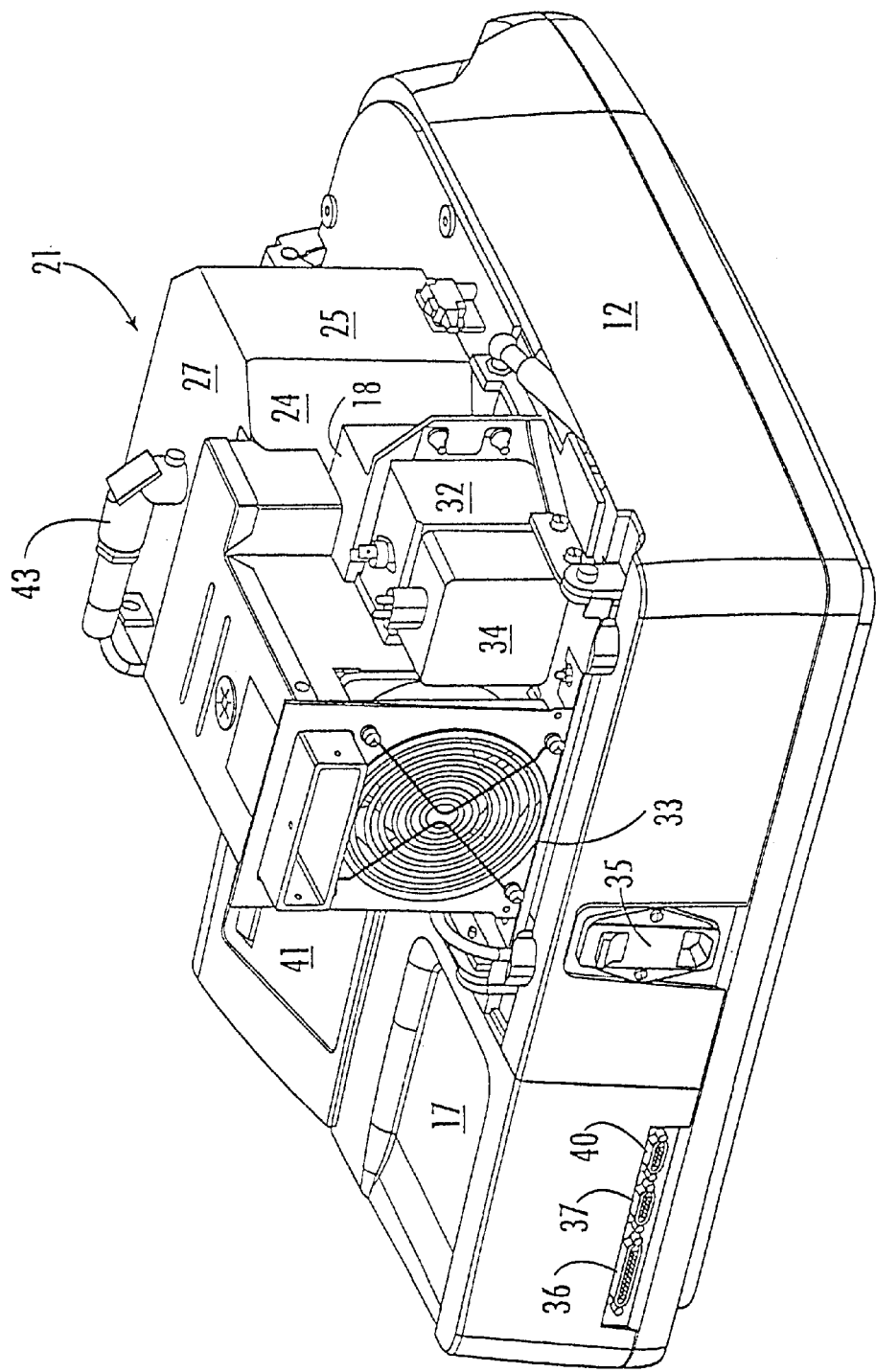
FIG. 4 is a view similar to FIG. 3 but taken from the opposite side of the volatiles analyzer.

FIG. 3 illustrates the source and waveguide as well as other aspects of the invention that have already been referred to. The source of microwave radiation typically comprises a magnetron illustrated at 32 in FIG. 3. The source can, however, comprise a klystron or a solid-state device. As noted earlier, the source 32 is in communication with the waveguide 23 which in turn is in communication with the cavity 21. FIG. 3 also illustrates a cooling system 33 which takes the form of a pan (FIG. 4).

FIG. 3 also illustrates that in preferred embodiments, the moisture analyzer includes an infrared sensor 34 positioned with respect to the cavity 21 to measure the temperature of a sample on the balance pan 20. The infrared sensor 43 is in electronic communication with means for moderating the microwave power in the cavity based upon the measured temperature. The moderation of temperature can be as simple as temporarily turning off the power from the magnetron 32, or it can be a more sophisticated control using, for example, a switching power supply. The basic use of the infrared sensor, and its advantages for processing certain types of items, are set forth in more detail in commonly assigned and copending application Ser. No. 09/156,086, filed Sep. 17, 1998, the contents of which are incorporated entirely herein by reference. The use of the switching power supply to control microwave energy is likewise set forth in co-pending and commonly assigned application Ser. No. 09/063,545, filed Apr. 21, 1998, which is likewise incorporated entirely herein by reference.

The moisture analyzer of the present invention typically further comprises a processor (not shown) in electronic communication with the balance for calculating the expected final weight of a sample based upon two or more measurements of the weight at discrete time intervals as the weight changes under the influence of microwave radiation upon the sample. The algorithms for calculating such final weight based on the weight change are generally well understood in this art and will not be set forth in detail herein. An early version is set forth, by way of example and not limitation, in U.S. Pat. Nos. 4,438,500 and 4,457,632, which are commonly assigned with the present application. Indeed, the use of particular algorithms and processor logic are often the choice of individual designers and can be carried out by those of ordinary skill in this art without undue experimentation. As another exemplary source, Dorf, *The Electrical Engineering Handbook, 2d Ed.* (CRC Press 1997), contains extensive discussions of electronic controls, circuits, and processor logic.

One of the advantageous features of the invention is its capacity of the cavity for supporting a plurality of TM and TE modes at the wavelengths produced by the source. As known to those of ordinary skill in this art, a mode is one of the various possible patterns of propagating or standing electromagnetic fields in a particular waveguide or cavity. A mode is characterized by its frequency, polarization, electric field strength, and magnetic field strength. The distribution of modes in a cavity will always satisfy Maxwell's equations and can be calculated to a fairly accurate extent, particularly using the available computational capacity of modern microprocessors. In the same manner, the term "field" is used in its usual sense to indicate the volume of influence of a physical phenomenon expressed as vectors. TM and TE modes refer to transverse electric and transverse magnetic modes. A transverse mode is one whose field vectors, whether electric or magnetic, are both normal to the direction of propagation of the wave energy.

The remainder of the figures illustrate these and other features of the invention. FIG. 4 illustrates the power supply 34 for the magnetron 32 as well as a clearer illustration of the pan 33. FIG. 4 also illustrates the power switch 35 which is also referred to as a power entry module. A series of sub-D connectors 36, 37, and 40, provide for optional communication with stand-alone printers or computers or similar devices. The sub-D connectors 36, 37, and 40 provide parallel and serial connections in a manner well understood by those of ordinary skill in these arts and the nature of the connections will not be otherwise explained in detail. FIG. 4 also illustrates the printer portion 41 of the device which, if desired, can take the results from any particular test, and print them out all on a paper tape. As just noted, the results can likewise be forwarded to digital memory, a digital processor, or any other location using the sub-D connectors. FIG. 4 also illustrates a number of the items which have already been described, and which carry corresponding numerals in FIG. 4, but which will not be otherwise described in detail.

Figure 5:
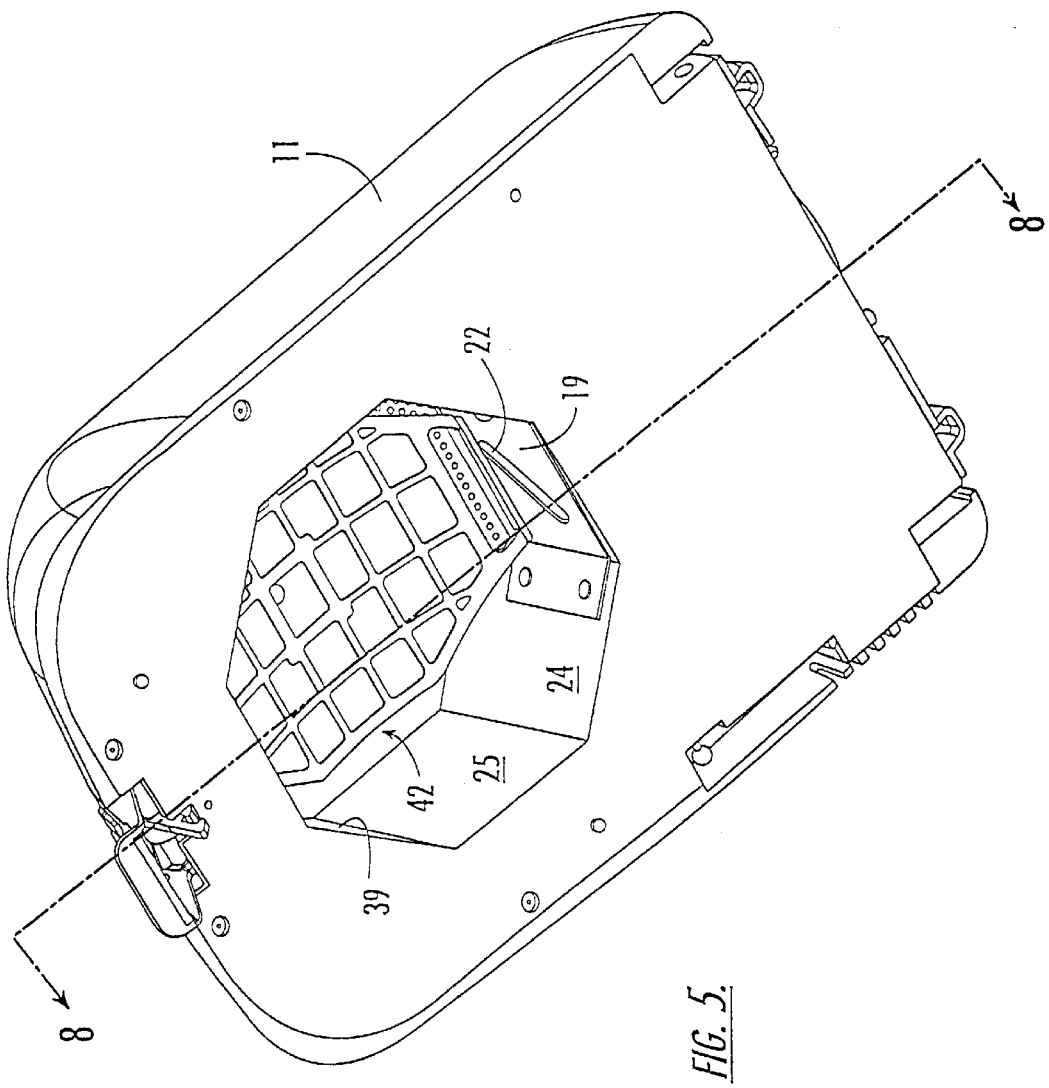
FIG. 5 is a perspective view taken into the upper portions of the cavity of the present invention.

FIG. 5 is a perspective view of the cover portion 11 of the analyzer 10, and showing a view looking upwards into the cavity 21. FIG. 5 illustrates the slot 22, the polyhedron shape of the cavity, and also illustrates the air shield 42 that is used in preferred embodiments of the invention. The nature, structure, function, and operation of the air shield 42 are set forth in greater detail in co-pending and commonly assigned application Ser. No. 09/397,825, filed concurrently herewith for "Microwave Apparatus and Method for Achieving Accurate Weight Measurements," the contents of which are incorporated entirely herein by reference.

Figure 6:
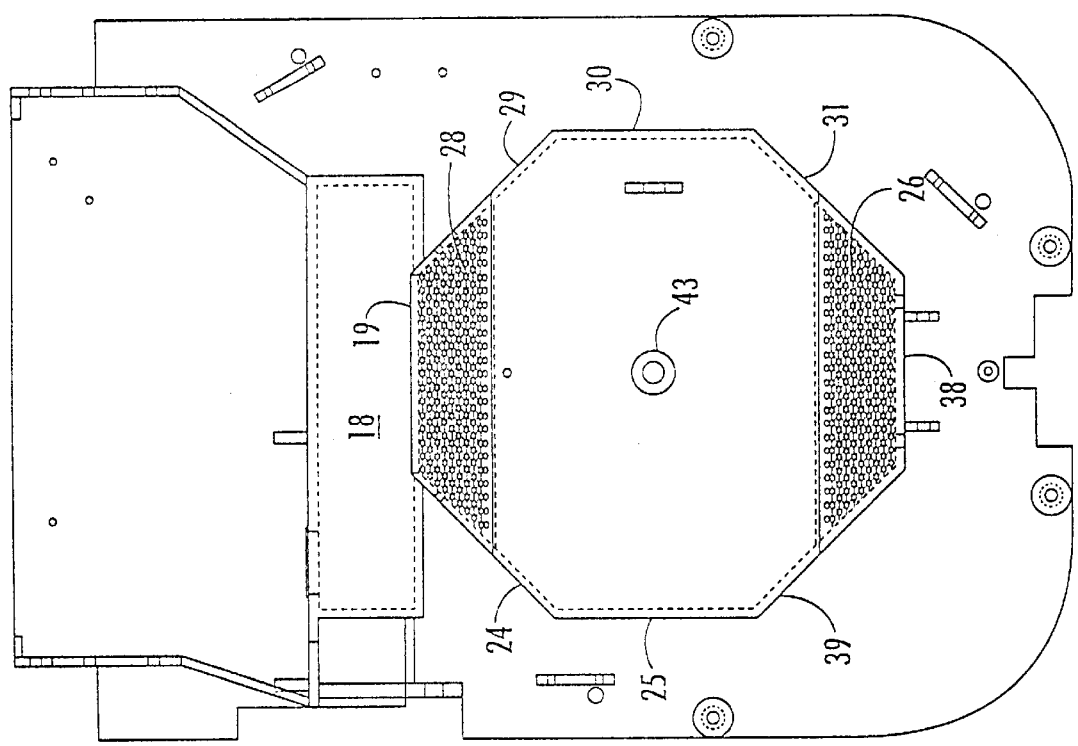
FIG. 6 is a top cross-sectional view taken along lines 6—6 of FIG. 3.

FIG. 6 is a top plan view of the cavity of the present invention and particularly illustrates the regular octagon shape of the bottom place 23 of the cavity, which in turn defines the cross-sectional shape of the cavity as taken from this view. FIG. 6 also shows the waveguide 18 adjacent to the cavity 21.

Figure 7:
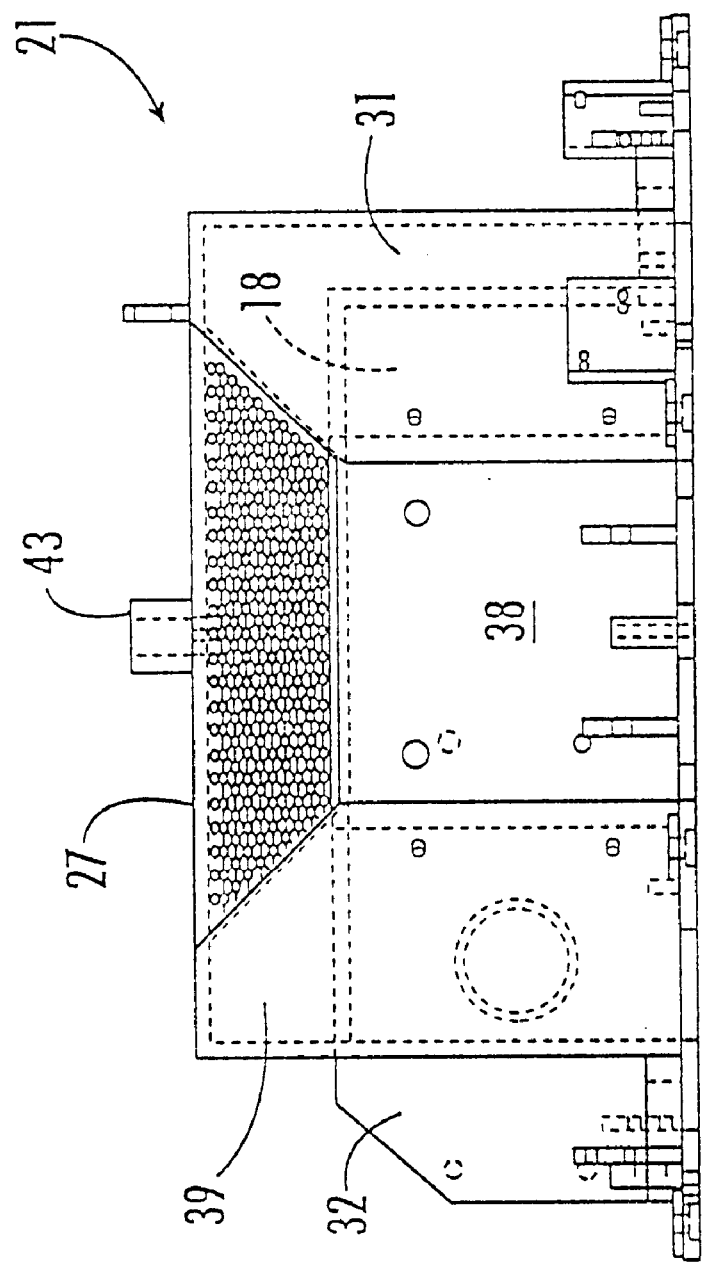
FIG. 7 is a front elevational view of the cavity according to the present invention.

FIG. 7 is a front elevational view of the cavity 21, and shows the perpendicular sides 19, 24, 25, 29–31, 38, and 39, as well as one of the nonparallel sides 26, which, in preferred embodiments of the invention, is perforated to allow for an airflow through the cavity 21 while the moisture analysis is taking place.

Figure 8:
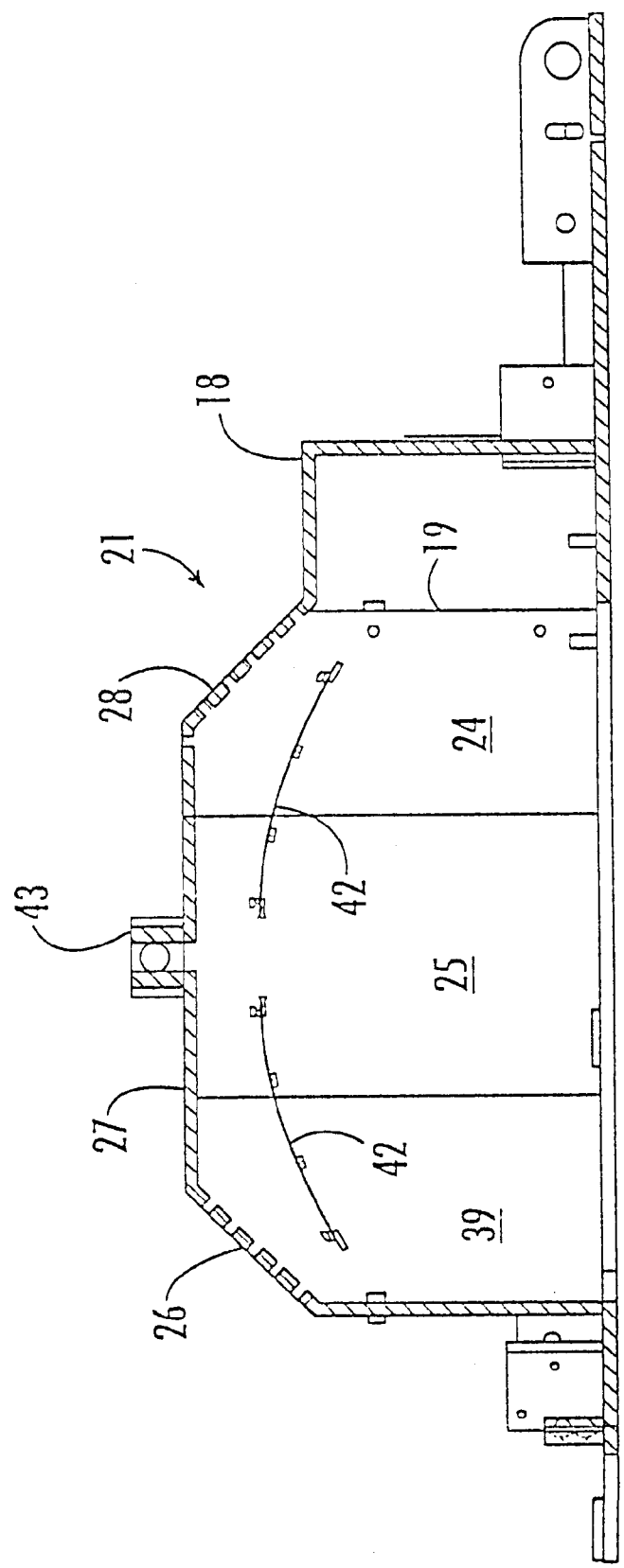
FIG. 8 is a cross-sectional view of the cavity taken along lines 8—8 of FIG. 5.

FIG. 8 is a cross-sectional view of the cavity 21 and showing the cross-sectional profile of the air shield 42 in one of its preferred positions.

Figure 9:
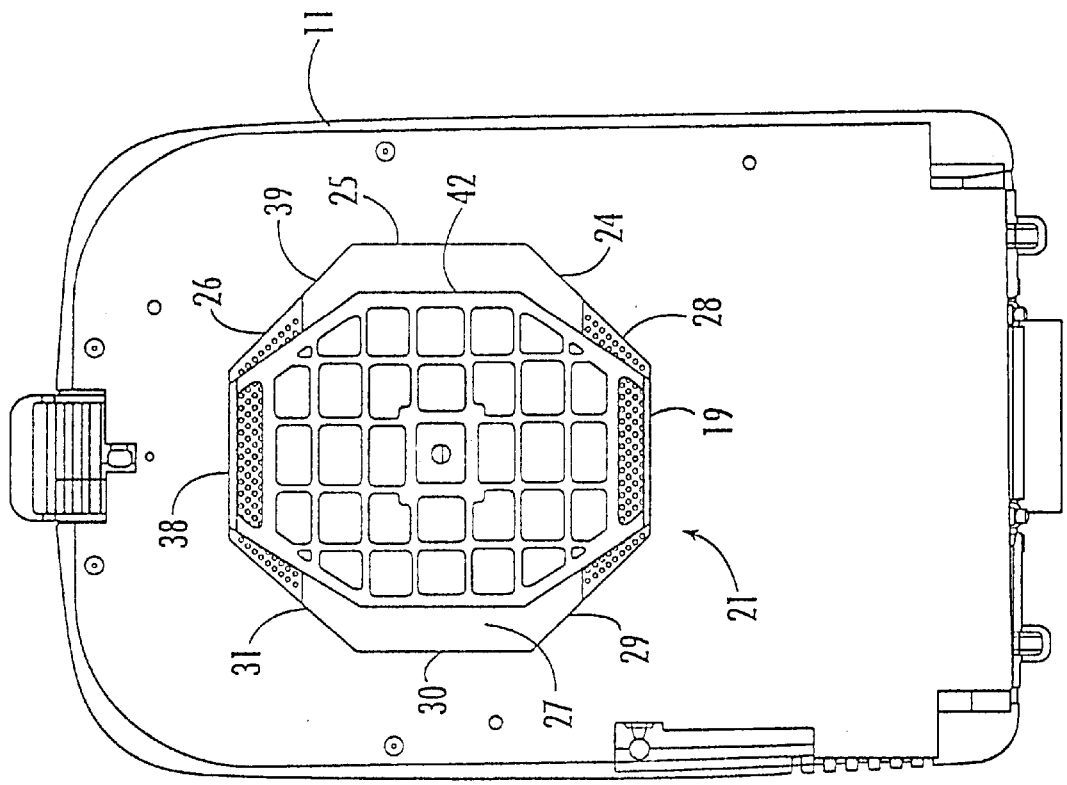
FIG. 9 is a bottom plan view of the top half of the lid and cavity of the present invention.

FIG. 9 is a bottom plan view of the cover portion 11, the cavity 21, and the air shield 42. FIG. 9 illustrates that both of the nonparallel, nonperpendicular sides are perforated to encourage the desired airflow, or airflow that can be enhanced using the fan 33.

Figure 10:
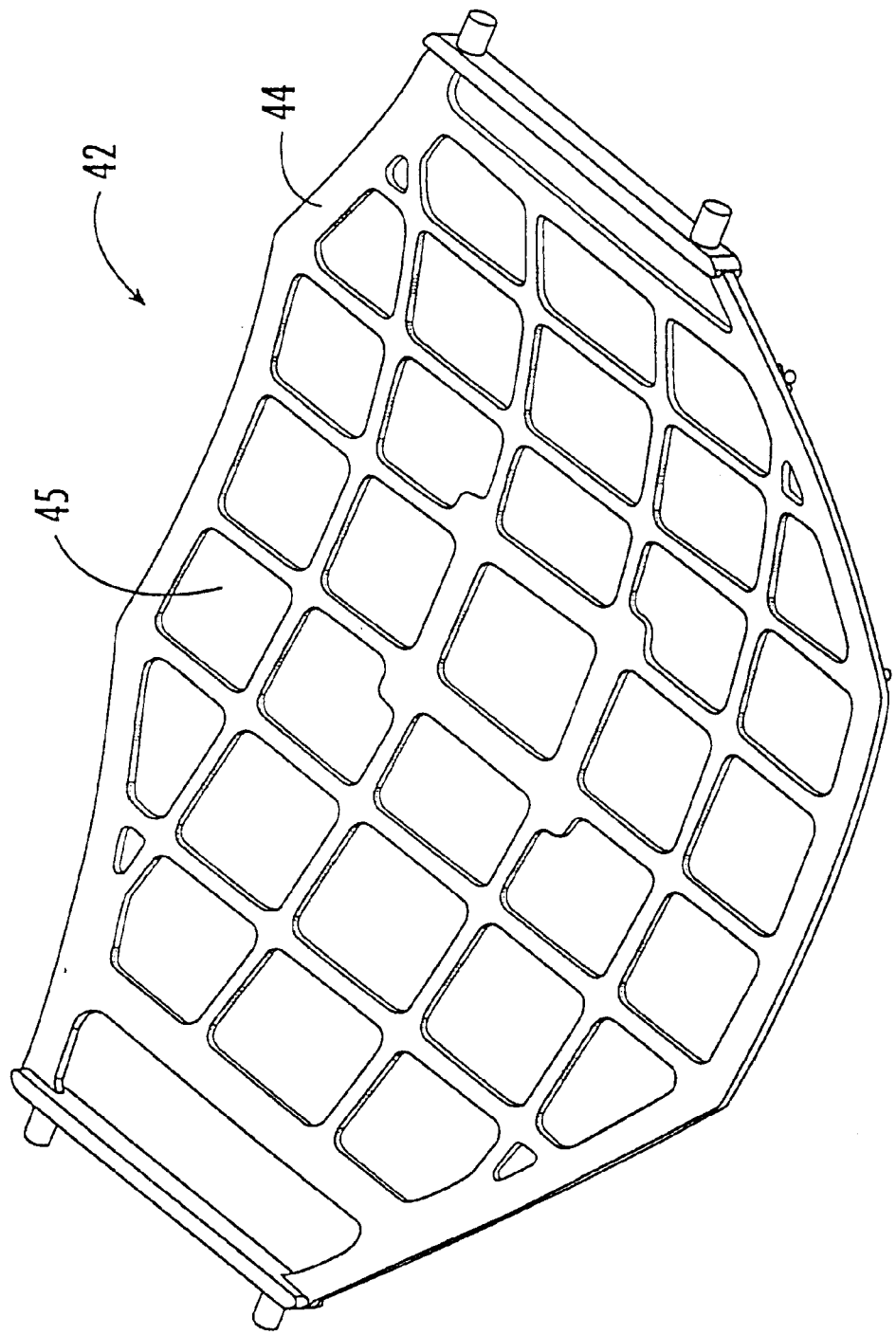
FIG. 10 is a perspective view of the air shield portion of the present invention.

FIG. 10 illustrates a preferred embodiment of the air shield 42 which is generally formed of a grid-like framework 44 which carries either a single, or a plurality of moisture absorbent pads 45. As set forth in the co-pending application, these pads absorb water vapor driven from a heated sample and allow it to recondense. By first absorbing the vapor, the shield 42 moderates the flow of gases through the cavity that could otherwise disturb the accuracy of the balance pan. Furthermore, as is known to those familiar with microwave techniques and characteristics, water vapor is affected differently by microwaves than liquid water and thus the absorbent pads provide a location where the water vapor can recondense, again be heated by the microwaves, and then be carried off by the fan. As set forth in the co-pending application, the fan preferably draws an airflow across the upper portions of the cavity 21 generally perpendicular to the expected flow of rising water vapor from the sample.

In this manner, the combination of the airflow and the shield help draw off the water vapor in a manner that disturbs the balance pan the least, and preferably not at all.

In the drawings and specification, there have been disclosed typical embodiments of the invention, and, although specific terms have been employed, they have been used in a generic and descriptive sense only and not for purposes of limitation, the scope of the invention being set forth in the following claims.

That which is claimed is:

1. A volatiles analyzer comprising:
   a source of microwave radiation that can selectively produce at least one predetermined frequency of microwave radiation;
   a cavity in communication with said source; and
   an analytical pan balance with at least its balance pan in said cavity; and wherein
   the walls of said cavity form a polyhedron having more than six faces and that focuses microwave energy of the predetermined frequency on said balance pan while supporting a plurality of TM and TE modes in said cavity.

2. A volatiles analyzer according to claim 1 further comprising:
   a waveguide between said source and said cavity and in microwave communication with both of said source and said cavity; and
   a port from said waveguide to said cavity.

3. A volatiles analyzer according to claim 1 wherein said port is the sole entry for microwaves between said waveguide and said cavity.

4. A volatiles analyzer according to claim 3 wherein:
   said waveguide is a rectangular solid; and
   said port is a longitudinal slot positioned in one face of said waveguide and oriented neither parallel to nor perpendicular to any of the angles forming said rectangular solid waveguide.

5. A volatiles analyzer according to claim 1 wherein all sides of said polyhedron cavity are planar.

6. A volatiles analyzer according to claim 5 wherein said polyhedron has 12 faces.

7. A volatiles analyzer according to claim 6 wherein the planes of eight of said twelve faces form a regular octagon.

8. A volatiles analyzer according to claim 7 wherein a second face of said polyhedron is an octagon parallel to said regular octagon face.

9. A volatiles analyzer according to claim 1 and further comprising:
   an infrared sensor positioned with respect to said cavity to measure the temperature of a sample on said balance pan;
   means in electronic communication with said infrared sensor for moderating the microwave power in said cavity based upon the measured temperature.

10. A volatiles analyzer according to claim 1 and further comprising a processor in electronic communication with said balance for calculating the expected final weight of a sample based upon two or more measurements of the weight at discrete time intervals as the weight changes under the influence of the microwave radiation upon the sample.

11. A volatiles analyzer according to claim 1 wherein said microwave source is selected from the group consisting of magnetrons, klystrons and solid state devices.

12. A volatiles analyzer comprising:
   a source of microwave radiation that can selectively produce at least one predetermined frequency of microwave radiation;
   a cavity in communication with said source;
   an analytical pan balance with at least its balance pan in said cavity; and
   said cavity comprising a polyhedron with more than eight faces and wherein the planes of eight of said faces form a regular octagon.

13. A volatiles analyzer according to claim 12 wherein said pokyhedron has 12 faces.

14. A volatiles analyzer according to claim 12 further comprising a waveguide in microwave communication with said source and said cavity.

15. A volatiles analyzer according to claim 14 wherein said waveguide communicates with said cavity through a single port.

16. A volatiles analyzer according to claim 15 wherein said port transmits a plurality of TM and TE modes, and said cavity supports a plurality of TM and TE modes.

17. A volatiles analyzer according to claim 16 wherein said cavity focuses the microwave energy on said balance pan.

18. A volatiles analyzer according to claim 12 wherein said cavity supports a plurality of TM and TE modes at the wavelengths produced by said source.

19. A volatiles analyzer according to claim 12 wherein said microwave source is selected from the group consisting of magnetrons, klystrons and solid state devices.

20. A volatiles analyzer according to claim 12 and further comprising a processor in electronic communication with said balance for calculating the expected final weight of a sample based upon two or more measurements of the weight at discrete time intervals as the weight changes under the influence of the microwave radiation upon the sample.

21. A volatiles analyzer according to claim 12 and further comprising:
   an infrared sensor positioned with respect to said cavity to measure the temperature of a sample on said balance pan;
   means in electronic communication with said infrared sensor for moderating the microwave power in said cavity based upon the measured temperature.

* * * * *